(12) United States Patent
Freese et al.

(10) Patent No.: US 8,879,053 B2
(45) Date of Patent: Nov. 4, 2014

(54) DEVICES HAVING AN INTEGRATED COMPUTATIONAL ELEMENT AND A PROXIMAL INTERFERENT MONITOR AND METHODS FOR DETERMINING A CHARACTERISTIC OF A SAMPLE THEREWITH

(75) Inventors: Robert Freese, Pittsboro, NC (US); Christopher Michael Jones, Houston, TX (US); David Perkins, The Woodlands, TN (US); Michael Simcock, Columbia, SC (US); William Soltmann, The Woodlands, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 159 days.

(21) Appl. No.: 13/456,259

(22) Filed: Apr. 26, 2012

(65) Prior Publication Data

US 2013/0287061 A1  Oct. 31, 2013

(51) Int. Cl.
| | |
|---|---|
| *G01N 21/00* | (2006.01) |
| *G01K 13/00* | (2006.01) |
| *G06E 3/00* | (2006.01) |
| *G01N 21/27* | (2006.01) |
| *G01N 21/17* | (2006.01) |

(52) U.S. Cl.
CPC ............... *G01N 21/17* (2013.01); *G01K 13/00* (2013.01); *G06E 3/001* (2013.10); *G01N 21/274* (2013.01); *G01N 2201/1215* (2013.01); *G01N 2201/1211* (2013.01); *G01N 2201/1214* (2013.01)
USPC .......................................................... 356/73

(58) Field of Classification Search
USPC .................................................... 356/72–73
See application file for complete search history.

(56) References Cited

U.S. PATENT DOCUMENTS

| | | |
|---|---|---|
| 3,488,491 A | 1/1970 | Schuman |
| 4,795,262 A | 1/1989 | Morris et al. |

(Continued)

FOREIGN PATENT DOCUMENTS

| | | |
|---|---|---|
| EP | 1061355 A1 | 12/2000 |
| EP | 1969326 | 9/2008 |

(Continued)

OTHER PUBLICATIONS

Myrick et al., "Application of Multivariate Optical Computing to Simple Near-Infrared Point Measurements," Proceedings of SPIE, US, vol. 4574, 2002, pp. 208-215, XP002391230.

(Continued)

*Primary Examiner* — Abdullahi Nur
(74) *Attorney, Agent, or Firm* — McDermott Will & Emery LLP; Craig W. Roddy

(57) ABSTRACT

The output of optical computing devices containing an integrated computational element can be corrected when an interferent substance or condition is present. The devices may comprise an optional electromagnetic radiation source; a sample detection unit comprising an integrated computational element and a detector configured to receive electromagnetic radiation that has optically interacted with the integrated computational element and produce a sample signal associated therewith; an interferent monitor located proximal to the sample detection unit, the interferent monitor being configured to produce an interferent signal associated with an interferent substance; and a signal processing unit operable to convert the interferent signal into an interferent input form suitable for being computationally combined with the sample signal, the signal processing unit being further operable to computationally combine the sample signal and the interferent input form to determine a characteristic of a sample in real-time or near real-time.

21 Claims, 5 Drawing Sheets

(56) References Cited

U.S. PATENT DOCUMENTS

| | | |
|---|---|---|
| 4,882,492 A | 11/1989 | Schlager |
| 5,737,076 A | 4/1998 | Glaus et al. |
| 6,091,504 A | 7/2000 | Walker et al. |
| 6,198,531 B1 | 3/2001 | Myrick et al. |
| 6,529,276 B1 | 3/2003 | Myrick |
| 7,123,844 B2 | 10/2006 | Myrick |
| 7,138,156 B1 | 11/2006 | Myrick et al. |
| 7,332,094 B2 | 2/2008 | Abney et al. |
| 7,472,748 B2 | 1/2009 | Gdanski et al. |
| 7,623,233 B2 | 11/2009 | Freese et al. |
| 7,697,141 B2 | 4/2010 | Jones et al. |
| 7,712,527 B2 | 5/2010 | Roddy |
| 7,834,999 B2 | 11/2010 | Myrick et al. |
| 7,911,605 B2 | 3/2011 | Myrick et al. |
| 7,920,258 B2 | 4/2011 | Myrick et al. |
| 7,934,556 B2 | 5/2011 | Clark et al. |
| 8,141,633 B2 | 3/2012 | Hampton et al. |
| 2002/0071121 A1 | 6/2002 | Ortyn et al. |
| 2007/0282647 A1 | 12/2007 | Freese et al. |
| 2008/0231849 A1 | 9/2008 | Myrick et al. |
| 2008/0276687 A1 | 11/2008 | Myrick et al. |
| 2009/0015819 A1 | 1/2009 | Van Beek et al. |
| 2009/0073433 A1 | 3/2009 | Myrick et al. |
| 2009/0097024 A1 | 4/2009 | Blackburn et al. |
| 2009/0137887 A1* | 5/2009 | Shariati et al. ............ 600/345 |
| 2009/0140144 A1 | 6/2009 | Myrick et al. |
| 2009/0154288 A1 | 6/2009 | Heathman |
| 2009/0182693 A1 | 7/2009 | Fulton et al. |
| 2009/0213380 A1 | 8/2009 | Appel et al. |
| 2009/0216504 A1 | 8/2009 | Priore et al. |
| 2009/0219512 A1 | 9/2009 | Myrick et al. |
| 2009/0219538 A1 | 9/2009 | Myrick et al. |
| 2009/0219539 A1 | 9/2009 | Myrick et al. |
| 2009/0250613 A1 | 10/2009 | Myrick et al. |
| 2009/0299946 A1 | 12/2009 | Myrick et al. |
| 2009/0316150 A1 | 12/2009 | Myrick et al. |
| 2010/0042348 A1 | 2/2010 | Bakker |
| 2010/0050905 A1 | 3/2010 | Lewis et al. |
| 2010/0051266 A1 | 3/2010 | Roddy et al. |
| 2010/0051275 A1 | 3/2010 | Lewis et al. |
| 2010/0073666 A1 | 3/2010 | Perkins et al. |
| 2010/0141952 A1 | 6/2010 | Myrick et al. |
| 2010/0149537 A1 | 6/2010 | Myrick et al. |
| 2010/0153048 A1 | 6/2010 | Myrick et al. |
| 2010/0182600 A1 | 7/2010 | Freese et al. |
| 2010/0195105 A1 | 8/2010 | Myrick et al. |
| 2010/0245096 A1 | 9/2010 | Jones et al. |
| 2010/0265509 A1 | 10/2010 | Jones et al. |
| 2010/0302539 A1 | 12/2010 | Myrick et al. |
| 2010/0305741 A1 | 12/2010 | Myrick |
| 2010/0328669 A1 | 12/2010 | Myrick et al. |
| 2011/0048708 A1 | 3/2011 | Glasbergen et al. |
| 2011/0163046 A1 | 7/2011 | Neal et al. |
| 2011/0199610 A1 | 8/2011 | Myrick et al. |
| 2012/0211650 A1 | 8/2012 | Jones et al. |
| 2013/0284894 A1 | 10/2013 | Freese et al. |
| 2013/0284895 A1 | 10/2013 | Freese et al. |
| 2013/0284896 A1 | 10/2013 | Freese et al. |
| 2013/0284897 A1 | 10/2013 | Freese et al. |
| 2013/0284898 A1 | 10/2013 | Freese et al. |
| 2013/0284899 A1 | 10/2013 | Freese et al. |
| 2013/0284900 A1 | 10/2013 | Freese et al. |
| 2013/0284901 A1 | 10/2013 | Freese et al. |
| 2013/0284904 A1 | 10/2013 | Freese et al. |
| 2013/0286398 A1 | 10/2013 | Freese et al. |
| 2013/0286399 A1 | 10/2013 | Freese et al. |

FOREIGN PATENT DOCUMENTS

| | | |
|---|---|---|
| EP | 2087328 | 8/2009 |
| EP | 2140238 | 1/2010 |
| EP | 2169384 A1 | 3/2010 |
| EP | 2320027 A1 | 5/2011 |
| WO | 2004057285 A1 | 7/2004 |
| WO | 2005064314 A1 | 7/2005 |
| WO | 2006021928 A1 | 3/2006 |
| WO | 2006110041 A1 | 10/2006 |
| WO | 2006114773 A1 | 11/2006 |
| WO | 2006137902 | 12/2006 |
| WO | 2007064575 | 6/2007 |
| WO | 2007098392 A2 | 8/2007 |
| WO | 2008057912 A2 | 5/2008 |
| WO | 2008057913 A2 | 5/2008 |
| WO | 2011063086 A1 | 5/2011 |
| WO | 2013162744 A1 | 10/2013 |
| WO | 2013162787 A1 | 10/2013 |
| WO | 2013162795 A1 | 10/2013 |
| WO | 2013162799 A1 | 10/2013 |
| WO | 2013162809 A1 | 10/2013 |
| WO | 2013162860 A1 | 10/2013 |
| WO | 2013162861 A1 | 10/2013 |
| WO | 2013162901 A1 | 10/2013 |
| WO | 2013162906 A1 | 10/2013 |
| WO | 2013162913 A1 | 10/2013 |
| WO | 2013162914 A1 | 10/2013 |

OTHER PUBLICATIONS

Nelson et al., "Multivariate Optical Computation for Predictive Spectroscopy," Analytical Chemistry, vol. 70, No. 1, 1998, pp. 73-82, XP055067630.

Bialkowski, "Species Discrimination and Quantitative Estimation Using Incoherent Linear Optical Signal Processing of Emission Signals," Analytical Chemistry, vol. 58, No. 12, 1986, pp. 2561-2563, XP055067237.

Medendorp, et al., "Applications of Interated Sensing and Processing Speciroscopic Imaging and Sensing," Journal of Chemometics, vol. 19, No. 10, 2006, pp. 533-542, XP055067235.

Bin Dai et al., "Molecular Factor Computing for Predictive Spectroscopy," Pharmaceutical Research, Kluwer Academic Publishers-Plenum Publishers, NL, vol. 24, No. 8, 2007, pp. 1441-1449, XP019507244.

International Search Report and Written Opinion for PCT/US2013/036177 dated Jun. 28, 2013.

International Search Report and Written Opinion for PCT/US2013/036107 dated Jun. 28, 2013.

International Search Report and Written Opinion for PCT/US2013/033975 dated Jun. 28, 2013.

International Search Report and Written Opinion for PCT/US2013/035572 dated Jun. 28, 2013.

International Search Report and Written Opinion for PCT/US2013035604 dated Jun. 28, 2013.

International Search Report and Written Opinion for PCT/US2013/031467 dated Jun. 28, 2013.

International Search Report and Written Opinion for PCT/US2013/031960 dated Jun. 28, 2013.

International Search Report and Written Opinion for PCT/US2013/032970 dated Jun. 28, 2013.

International Search Report and Written Opinion for PCT/US2013/033256 dated Jun. 28, 2013.

International Search Report and Written Opinion for PCT/US2013/033502 dated Jun. 28, 2013.

Sullivan et al. "Implementation of a Numerical Needle Method for Thin-Film Design," Applied Optics, vol. 35, No. 28, pp. 5484-5492, 1996.

Dobrowolski et al., "Refinement of Optical Multilayer Systems with Different Optimization Procedures," Applied Optics, vol. 29, No. 19, pp. 3876-2893, 1990.

Myrick, et al. "Spectral Tolerance Determination for Multivariate Optical Element Design," Fresenius' Journal of Analytical Chemistry, 369:2001; pp. 351-355.

Gdanski et al., "A New Model for Matching Fracturing Fluid Flowback Composition," 2007 SPE Hydraulic Fracturing Technology Conference held in College Station, Texas, SPE 106040.

Gdanski et al., "Using Lines-of-Solutions to Understand Fracture Conductivity and Fracture Cleanup," SPE Production and Operations Symposium held in Oklahoma City, OK, 2011, SPE 142096.

(56) References Cited

OTHER PUBLICATIONS

Qu et al, "Fluorescence Spectral Imaging for Characterizaton of Tissue Based on Multivariate Statistical Analysis," Journal of the Optical Society of American, vol. 19, No. 9, 2002 XP055046065.

International Search Report and Written Opinion for PCT/US2013/036287 dated Aug. 2, 2013.
International Search Report and Written Opinion for PCT/US2013/036294 dated Aug. 7, 2013.

* cited by examiner

US 8,879,053 B2

DEVICES HAVING AN INTEGRATED COMPUTATIONAL ELEMENT AND A PROXIMAL INTERFERENT MONITOR AND METHODS FOR DETERMINING A CHARACTERISTIC OF A SAMPLE THEREWITH

BACKGROUND

The present disclosure relates to devices and methods for determining a characteristic of a sample using an integrated computational element, and, more specifically, to devices and methods that can correct a signal received from an integrated computational element in the presence of one or more interferent substances or interferent conditions.

Spectroscopic techniques for measuring various characteristics of materials are well known and routinely used under laboratory conditions. In cases where there is not extensive sample matrix interference, spectroscopic techniques can sometimes be carried out without using an involved sample preparation. It is more common, however, to carry out various sample preparation procedures before conducting the analysis. Reasons for conducting sample preparation procedures before carrying out an analysis can include, for example, removing interferent substances from the sample, converting an analyte of interest into a chemical form that can be better detected by a chosen spectroscopic technique, concentrating a low concentration analyte, and/or adding standards to improve the accuracy of quantitative measurements. Sample preparation steps can result in delays of hours to days when obtaining an analysis. Furthermore, there can be additional delays associated with transporting the sample to a laboratory equipped to carry out the analysis.

Although spectroscopic techniques can, at least in principle, be conducted at a job site in real-time or near real-time, the transitioning of spectroscopic instruments from the laboratory into a field or process environment can be expensive and complex. For example, conditions such as inconsistent temperature, humidity, and vibration can be commonly encountered during field or process use, and they can be difficult to compensate for with conventional spectroscopic instruments. At a minimum, these conditions and others can affect the calibration and durability of many types of spectroscopic instruments. Further, field personnel may not have the training needed to satisfactorily carry out a spectroscopic analysis and take appropriate action in response.

As an alternative to conventional spectroscopic techniques, optical computing devices containing an integrated computational element can be configured to specifically detect a characteristic of interest in a sample. Optical computing devices may utilize electromagnetic radiation to perform calculations, as opposed to the hardwired circuits of conventional electronic processors. Because optical computing devices can be specifically configured to detect a characteristic of interest, there may sometimes be a reduced need to conduct involved sample preparation steps prior to conducting an analysis. Further, optical computing devices are generally operationally simple and rugged. Thus, optical computing devices may be less impacted by the conditions that degrade the performance of conventional spectroscopic instruments, thereby making them well suited for field or process environments.

Unlike conventional spectroscopic instruments, which produce a spectrum that needs further interpretation to obtain a result, the ultimate output of an optical computing device is a real number that can be correlated with a characteristic of a sample. Correlation of the output of an optical computing device to a sample characteristic may be conducted, for example, by comparing the device's output for a sample against the device's output for one or more standards having a known value of a characteristic of interest or a function derived therefrom. The output simplicity of optical computing devices is one of their more desirable features, which allows them to be deployed with little or no operator training.

Although optical computing devices may be less impacted by interfering environmental and sample conditions than are conventional spectroscopic instruments, there often remains a need to monitor for the presence of interferent substances or interferent conditions, particularly when analyzing samples that have not undergone further sample preparation steps. For example, an optical computing device may have only been confirmed to provide a response that is representative of a characteristic of interest within a specified calibration range. Outside this calibration range, an interferent substance or condition may alter the response of the optical computing device such that its output is no longer representative of a sample's characteristic, for example. Interferent substances or conditions may undesirably interact with any component of an optical computing device, including its integrated computational element and/or electronic components associated therewith, to alter its response. In other cases, a sufficient amount of an interferent substance within or near a sample may change or block a spectral absorbance related to a characteristic of interest. Any of these events may result in a breadth of outcomes, ranging from questionable data integrity to complete data unintelligibility. In the case of certain field and process operations, questionable and/or lost data can present serious financial consequences and impact the ability to perform a job or evaluate the effectiveness of a job.

SUMMARY OF THE INVENTION

The present disclosure relates to devices and methods for determining a characteristic of a sample using an integrated computational element, and, more specifically, to devices and methods that can correct a signal received from an integrated computational element in the presence of one or more interferent substances or interferent conditions.

In some embodiments, the present invention provides a device comprising: an optional electromagnetic radiation source; a sample detection unit comprising an integrated computational element and a detector that is configured to receive electromagnetic radiation that has optically interacted with the integrated computational element and produce a sample signal associated therewith; an interferent monitor located proximal to the sample detection unit, the interferent monitor being configured to produce an interferent signal associated with an interferent substance; and a signal processing unit that is operable to convert the interferent signal into an interferent input form suitable for being computationally combined with the sample signal, the signal processing unit being further operable to computationally combine the sample signal and the interferent input form to determine a characteristic of a sample in real-time or near real-time.

In some embodiments, the present invention provides a device comprising: an optional electromagnetic radiation source; a sample detection unit comprising a first integrated computational element and a detector that is configured to receive electromagnetic radiation that has optically interacted with the first integrated computational element and produce a sample signal associated therewith; an interferent monitor located proximal to the sample detection unit, the interferent monitor comprising a second integrated computational element and being configured to produce an interferent signal associated with an interferent substance or an interferent condition; an optional data storage unit that is operable to record the sample signal and the interferent signal as a function of time; and a signal processing unit that is operable to convert the interferent signal into an interferent input form suitable for being computationally combined with the sample signal, the signal processing unit being further operable to computationally combine the sample signal and the interferent input form to determine a characteristic of a sample.

In some embodiments, the present invention provides a method comprising: providing electromagnetic radiation that has optically interacted with or that has been emitted by a sample; providing a sample detection unit comprising a first integrated computational element and a detector configured to receive electromagnetic radiation that has optically interacted with the first integrated computational element; optically interacting electromagnetic radiation with the first integrated computational element; detecting the electromagnetic radiation that has optically interacted with the first integrated computational element, thereby producing a sample signal associated therewith; monitoring an interferent substance using an interferent monitor and producing an interferent signal associated therewith; converting the interferent signal into an interferent input form suitable for being computationally combined with the sample signal; computationally combining the sample signal and the interferent input form so as to produce a combined signal; and correlating the combined signal to a characteristic of the sample in real-time or near real-time.

The features and advantages of the present invention will be readily apparent to one having ordinary skill in the art upon a reading of the description of the preferred embodiments that follows.

BRIEF DESCRIPTION OF THE DRAWINGS

The following figures are included to illustrate certain aspects of the present invention, and should not be viewed as exclusive embodiments. The subject matter disclosed is capable of considerable modification, alteration, and equivalents in form and function, as will occur to one having ordinary skill in the art and having the benefit of this disclosure.

DETAILED DESCRIPTION

Figure 1:
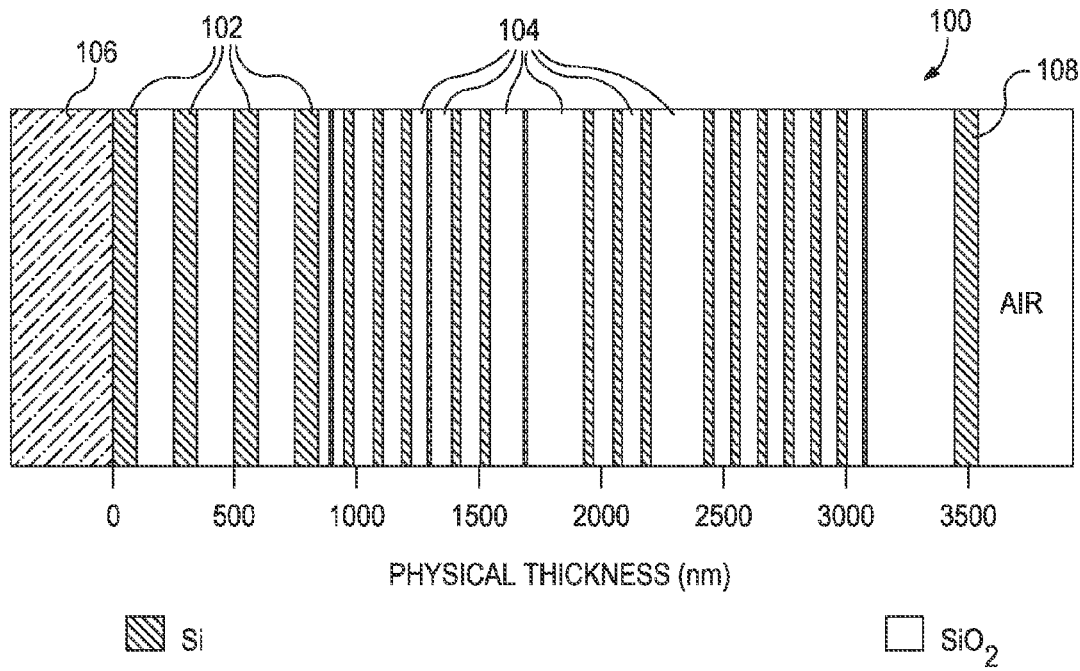
FIG. 1 shows a schematic of an illustrative integrated computational element (ICE).

The present disclosure relates to devices and methods for determining a characteristic of a sample using an integrated computational element, and, more specifically, to devices and methods that can correct a signal received from an integrated computational element in the presence of one or more interferent substances or interferent conditions.

Although the output simplicity of optical computing devices (i.e., a real number) is one of their strengths, this feature has heretofore limited one's ability to evaluate and correct the output when one or more interferents are present. As used herein, the term "interferent" refers to a substance or condition that changes the output of an optical computing device when evaluating a characteristic of interest in a sample. As used herein, the term "interferent substance" refers to a material that, when present, alters the sample signal associated with an optical computing device. As used herein, the term "interferent condition" refers to a state within or near an optical computing device that, when present, alters its sample signal (e.g., temperature and pressure). It is to be understood that the mechanism by which an interferent produces interference in an analysis is not particularly limited. In the case of conventional spectroscopic techniques, interfering substances can sometimes be dealt with through spectral deconvolution techniques that remove an interferent signal from a spectrum. Optical computing techniques, in contrast, have not availed a like capability, since there is no spectrum to deconvolute.

In the present disclosure, we describe that an interferent signal can be computationally combined with a sample signal associated with a characteristic of interest to correct for the presence of the interferent. Any type of interference (e.g., electronic interference, magnetic interference, optical pathway interference, spectral interference, and the like) may be corrected using the devices and methods described herein. Moreover, the correction may be made in real-time or near real-time without resorting to time consuming post-analysis data recovery procedures to determine a characteristic of a sample.

In many instances when analyzing a characteristic of a sample using an optical computing device containing an integrated computational element, the presence of one or more interferents can radically change the output of the device, often in an unpredictable way. As a result, it is not infrequent that the correction factor needed to correct the output of the device is of the same magnitude of the device output itself, particularly for characteristics that produce a low detector response. Ordinarily, when applying a correction factor of such large magnitude, one would not expect to be able to extract reliable data from a corrected signal due to error propagation and noise. However, in the embodiments described herein, even when correction factors having a significant magnitude relative to that of a sample signal are employed, useful results may still be obtained after correction. Further discussion of how the correction factors are determined and applied in the present embodiments is described in further detail below.

When utilizing optical computing devices in a particular type of application, an operator may many times be aware a priori of the types of interferents that may be present. These interferents may interact differently with any component of the optical computing device to impact its output. For example, an interferent substance may block an optical pathway or otherwise strongly absorb, transmit, reflect, or scatter electromagnetic radiation that would otherwise optically interact with a sample. Furthermore, an interferent may alter the output of electronic components associated with an optical computing device, in addition to directly changing the output of an integrated computational element itself. Without monitoring for interferents in some manner, an operator would have no way to determine if a change in the sample signal was associated with a true change in the value of a characteristic, a change in intensity from an electromagnetic radiation source, blocking of an optical pathway, a change in the performance of an electronic component, or any combination thereof. As discussed previously, without further information, this uncertainty can lead to the inability to successfully interpret data received from a job and/or proactively manage a job. Loss of data and/or making decisions based upon faulty data can have significant and costly ramifications in many fields, including the oil and gas industry, for example.

In addition to providing the useful ability to recover and correct data, the devices and methods described herein can significantly simplify the construction and design of the integrated computational element(s) employed therein. As previously described, integrated computational elements are typically fabricated so as to be specifically configured for analyzing a characteristic of interest. Although, at least in principle, integrated computational elements may be fabricated with capabilities for analyzing a characteristic of interest in the presence of an interferent, this feature undoubtedly increases the complexity associated with their construction. For example, commonly assigned U.S. Pat. No. 7,911,605 and United States Patent Application Publication 20100153048, each of which is incorporated herein by reference in its entirety, describe in great detail how to design and construct integrated computational elements having a desired performance for a single characteristic of interest. The theory behind optical computing and the operation of conventional optical computing devices is described in more detail in the following commonly owned United States patents and United States patent application Publications, each of which is incorporated herein by reference in its entirety: U.S. Pat. Nos. 6,198,531, 6,529,276, 7,123,844, 7,834,999, 7,911,605, 7,920,258, 20090219538, 20090219539, and 20090073433. Accordingly, the theory behind optical computing will not be discussed in any detail herein unless needed to better describe one or more embodiments of the present disclosure.

Interferents can be monitored with conventional sensors, integrated computational element(s), or any combination thereof according to the embodiments described herein. The interferent signal so obtained can be converted into an interferent input form (i.e., a correction factor) that is suitable for being computationally combined with a sample signal associated with a characteristic of interest, as determined using an integrated computational element. Applicant does not believe that there has been any recognition or suggestion in the art to computationally combine the output of an integrated computational element in order to correct its output, particularly in view of the significant corrections that are often needed with these systems, as discussed above.

Although conventional optical computing devices containing multiple integrated computational elements have been heretofore described, the integrated computational elements of conventional optical computing devices are believed to have been configured to operate essentially independently of one another to analyze a single characteristic per integrated computational element. Applicant does not believe that there has been any prior recognition or suggestion in the art to computationally combine the output of two or more integrated computational elements to obtain a useful result. As disclosed in commonly assigned U.S. patent application Ser. Nos. 13/456,255, 13/456,264, 13/456,283, 13/456,350, 13/456,405, and Ser. No. 13/456,467 each filed concurrently herewith and incorporated herein by reference in its entirety, and now available, respectively, as U.S. Patent Application Publications 2013/0284894, 2013/0284895, 2013/0284896, 2013/0284899, 2013/02849404 and 2013/0286399,Applicant has discovered that the output of two or more integrated computational elements may be computationally combined to result in surprising improvements in detection performance for a single characteristic of interest. These benefits are significant and may be greater than additive in some cases. Furthermore, as disclosed in the co-pending applications, these benefits may be realized when the two or more integrated computational elements are associated with the characteristic of interest, disassociated with the characteristic of interest, or any combination thereof. It is particularly surprising that a disassociated integrated computational element may be beneficially utilized to determine a characteristic of interest, since it was heretofore believed that it was desirable for the integrated computational element to be associated with the characteristic of interest. In addition to the foregoing, combinations of integrated computational elements where at least one of the integrated computational elements demonstrates a positive response and at least one of the integrated computational elements demonstrates a negative response as the value of a characteristic increases may result in related surprising and beneficial improvements as well.

In the present disclosure, we have further expanded upon the concept of computationally combining the output of an integrated computational element to obtain a useful result. As discussed above, the output of an integrated computational element may be corrected by computationally combining an interferent input form that is suitable for being computationally combined therewith (i.e., a correction factor). The interferent input form may be derived from a conventional sensor and/or from another integrated computational element configured to analyze for an interferent substance.

Fundamentally, the value of a characteristic of interest may be expressed by Formulas (1) or (2), where $C_{true}$ is the true value of the characteristic, $C_{obs}$ is the observed value of the characteristic, and $K(I_1, I_2, \ldots I_n)$ a correction factor. Correction factor K is a complex, multivariate function that may be dependent upon an amount of each interferent $I_n$ that is present, as well as the true value of the characteristic being measured. Depending upon how one wishes to express correction factor K, the correction may be expressed by a difference as in Formula (1) or as a product as in Formula (2).

$$C_{true} = C_{obs} - K(C_{true}, I_1, I_2, \ldots I_n) \tag{1}$$

$$C_{true} = (C_{obs})K(C_{true}, I_1, I_2, \ldots I_n) \tag{2}$$

To determine correction factor K, the output of the devices may be evaluated in the presence of varying concentrations and combinations of the interferents that are anticipated to be present in the analysis. Varying values of the characteristic to be determined are also included in these measurements. These measurements are prior to conducting an analysis for a characteristic having an unknown value in a sample. Correction factor K may be expressed as a lookup table in some embodiments. Ideally, the data measured as described above may be fit through appropriate curve fitting techniques as a multivariate function so as to not have to rely upon making a comparison using the discrete values of a lookup table. Data from determining correction factor K may be coupled to an appropriate signal processing unit to enable determination of the true value of a characteristic of interest in a sample. Coupling the data to an appropriate signal processing unit may allow real-time or near-real time determination of the characteristic to be made. Both interferent substances and interferent conditions may be included in the correction factor, if desired.

Optical computing devices employing an integrated computational element may be used to analyze various types of samples. One particular class of samples that may be analyzed by the devices and methods described herein are those that are commonly encountered in the oil and gas industry. Oil and gas samples, treatment fluids used in conjunction with the oil and gas industry, and produced fluids from a subterranean formation, for example, may be very complex and difficult to assay by conventional spectroscopic techniques, particularly without conducting detailed sample preparation. Uses of conventional optical computing devices in the analysis of fluids and other materials commonly encountered in the oil and gas industry are described in commonly owned U.S. patent application Ser. Nos. 13/198,915, 13/198,950, 13/198,972, 13/204,005, 13/204,046, 13/204,123, 13/204,165, 13/204,213, and 13/204,294, each filed on Aug. 5, 2011 and incorporated herein by reference in its entirety. In particular, the optical computing devices described herein may be used in any of the drilling phase, the stimulation phase, the production phase, and/or the remediation phase of subterranean operations. Illustrative materials that may be analyzed include, for example, treatment fluids (e.g., drilling fluids, acidizing fluids, fracturing fluids, and the like), pipeline fluids, bacteria, carrier fluids, source materials, produced water, produced hydrocarbon fluids, subterranean surfaces, and the like. Without limitation, the optical computing devices described herein may be used to assay, for example, the composition and properties of a hydrocarbon fluid within or being produced from a subterranean formation (e.g., water content, gas-oil ratio, and the like), a treatment fluid being introduced to or within a subterranean formation, a spent or partially spent treatment fluid being produced from a subterranean formation, water being produced from a subterranean formation, a subterranean surface, and/or a pipeline surface. One of ordinary skill in the art will appreciate that information regarding the composition and properties of these materials and others may provide valuable insight into the progress and outcome of a subterranean operation. Optical computing devices, including those described herein, provide a relatively low cost, rugged, and accurate system that can be used to analyze one or more characteristics of these type of samples and others. It will be appreciated, however, that the various devices disclosed herein may be used in other technology fields including, for example, the food and drug industry, industrial applications, mining industries, or any field where it may be advantageous to determine a characteristic of a sample in real-time or near real-time.

As used herein, the term "sample" and variations thereof refer to at least a portion of a substance of interest to be tested or otherwise evaluated using the optical computing devices described herein. The sample may possess a characteristic of interest. The sample may be any fluid or any solid substance or material such as, but not limited to, rock formations, concrete, and like solid surfaces.

As used herein, the term "fluid" refers to any substance that is capable of flowing, including particulate solids, liquids, gases, slurries, emulsions, powders, muds, glasses, any combination thereof, and the like. In some embodiments, the fluid can be an aqueous fluid, including water, mixtures of water and water-miscible fluids, and the like. In some embodiments, the fluid can be a non-aqueous fluid, including organic compounds (i.e., hydrocarbons, oil, a refined component of oil, petrochemical products, and the like). In some embodiments, the fluid can be a treatment fluid or a formation fluid. Illustrative gases that can be present in fluids include, for example, air, nitrogen, carbon dioxide, argon, helium, hydrogen sulfide, mercaptans, methane, ethane, propane, butane, other hydrocarbon gases, combinations thereof, and the like.

As used herein, the term "treatment fluid" refers to a fluid that is placed in a subterranean formation or in a pipeline in order to perform a desired function. Treatment fluids can be used in a variety of subterranean operations, including, but not limited to, drilling operations, production treatments, stimulation treatments, remedial treatments, fluid diversion operations, fracturing operations, secondary or tertiary enhanced oil recovery (EOR) operations, and the like. As used herein, the terms "treat," "treatment," "treating," and other grammatical equivalents thereof refer to any operation that uses a fluid in conjunction with performing a desired function and/or achieving a desired purpose. The terms "treat," "treatment," and "treating," as used herein, do not imply any particular action by the fluid or any particular component thereof unless otherwise specified. Treatment fluids for subterranean operations can include, for example, drilling fluids, fracturing fluids, acidizing fluids, conformance treatment fluids, damage control fluids, remediation fluids, scale removal and inhibition fluids, chemical floods, and the like.

As used herein, the term "characteristic" refers to a chemical, mechanical, or physical property of a substance. A characteristic of a substance may include a quantitative value of one or more chemical components therein. Such chemical components may be referred to as "analytes." Illustrative characteristics of a substance that can be monitored with the optical computing devices disclosed herein include, for example, chemical composition (identity and concentration, in total or of individual components), impurity content, pH, viscosity, density, ionic strength, total dissolved solids, total particulate solids, salt content, porosity, opacity, bacteria content, any combination thereof, and the like.

As used herein, the term "electromagnetic radiation" refers to radio waves, microwave radiation, infrared and near-infrared radiation, visible light, ultraviolet radiation, X-ray radiation, and gamma ray radiation.

As used herein, the term "optical computing device" refers to an optical device containing an integrated computational element that is configured to receive an input of electromagnetic radiation (e.g., from a substance or sample of the substance) and produce an output of electromagnetic radiation that is changed in some way so as to be readable by a detector, such that an output of the detector can be correlated with at least one characteristic of the substance. The output of electromagnetic radiation from the integrated computational element can be reflected electromagnetic radiation, transmitted electromagnetic radiation, and/or dispersed electromagnetic radiation. As will be appreciated by one having ordinary skill in the art, whether reflected, dispersed, or transmitted electromagnetic radiation is analyzed by a detector will be dictated by numerous experimental factors that will be dependent on the chosen application (e.g., the type of sample and optical transparency of the sample being analyzed). In addition, emission and/or scattering of a sample (e.g., via fluorescence, luminescence, Raman scattering, and/or Raleigh scattering) can also be monitored by the optical computing devices.

As used herein, the term "optically interact" and variations thereof refer to the reflection, transmission, scattering, diffraction, or absorption of electromagnetic radiation by an integrated computational element or a sample. Accordingly, the term "optically interacted electromagnetic radiation" refers to electromagnetic radiation that has been reflected, transmitted, scattered, diffracted, or absorbed by, or emitted, or re-radiated from an integrated computational element or a sample.

As used herein, the term "proximal" refers to the state of two objects being located sufficiently close to one another that they are exposed to substantially the same conditions.

As used herein, the terms "real-time" and "near real-time" refer to a determination of a sample characteristic that takes place concurrently with the analysis of the sample. That is, a "real-time" or "near real-time" determination of a sample characteristic does not take place offline after data sampling using post-acquisition processing techniques. A result that is returned in "real-time" may be returned essentially instantaneously. A "near real-time" result is returned after a brief delay, which may be associated with processing time, further data acquisition for determining a characteristic, and the like. It will be appreciated by one having ordinary skill in the art that the rate at which a sample characteristic is determined in "real-time" or "near real-time" may be dependent upon the processing speed associated with a signal processing unit and the rate at which data is collected.

As used herein, the term "sealed container" refers to an enclosure containing a fixed environment that is prevented from intermingling with its surrounding environment.

As used herein, the term "computationally combine" and variants thereof refer to the sum, difference, product, or quotient of the raw output of an optical computing device and a correction factor determined for the optical computing device in the presence of one or more interferents. The correction factor may be determined as described above.

The devices described herein may employ one or more integrated computational elements in the course of determining a characteristic of interest in a sample. A brief description of an illustrative integrated computational element follows below. Further details regarding integrated computational elements may be found, for example, in commonly owned U.S. Pat. No. 6,198,531, previously incorporated by reference in its entirety.

FIG. 1 shows a schematic of an illustrative integrated computational element (ICE) 100. As illustrated in FIG. 1, ICE 100 may include a plurality of alternating layers 102 and 104, such as silicon (Si) and $SiO_2$ (quartz), respectively, for example. In general, layers 102 and 104 contain materials whose indices of refraction are high and low, respectively. Other illustrative examples may include niobia and niobium, germanium and germania, MgF, and SiO. Additional materials having high and low indices of refraction can be envisioned by one having ordinary skill in the art, and the composition of layers 102 and 104 is not considered to be particularly limited. Layers 102 and 104 may be strategically deposited on optical substrate 106. In some embodiments, optical substrate 106 may be BK-7 optical glass. In other embodiments, optical substrate 106 may be formed from other types of optical materials such as, for example, quartz, sapphire, silicon, germanium, zinc selenide, zinc sulfide, various polymers (e.g., polycarbonates, polymethylmethacrylate, polyvinylchloride, and the like), diamond, ceramics, and the like. Opposite to optical substrate 106, ICE 100 may include layer 108 that is generally exposed to the environment of the device or installation in which it is used. The number and thickness of layers 102 and 104 may be determined based upon the spectral attributes of a sample characteristic acquired from via conventional spectroscopic analyses using a suitable spectroscopic instrument. For a given characteristic, a conventional spectrum may include one or more ranges of wavelengths that are uniquely influenced by that characteristic. It should be understood that illustrative ICE 100 of FIG. 1 has been presented for purposes of illustration only. Thus, it is not implied that ICE 100 is predictive for any particular characteristic of a given sample, nor do the number and thicknesses of layers 102 and 104 bear correlation to any particular characteristic of a given sample. Further, layers 102 and 104 are not necessarily drawn to scale and should therefore not be considered as limiting of the present disclosure. Moreover, one having ordinary skill in the art will readily recognize that the materials comprising layers 102 and 104 may vary depending on factors such as, for example, the application, cost of materials, and/or applicability of the material to the sample substance.

In some embodiments, the material within layers 102 and 104 can be doped, or two or more materials can be combined in a manner to achieve a desired optical response. In addition to solids, the ICE 100 may also contain liquids (e.g., water) and/or gases, optionally in combination with solids, in order to produce a desired optical response. In the case of gases and liquids, ICE 100 can contain a corresponding vessel (not shown) which houses the gases or liquids. Additional exemplary variations of ICE 100 may also include, for example, holographic optical elements, gratings, piezoelectric elements, light pipe, digital light pipe (DLP), and/or acousto-optic elements, for example, that can create transmission, reflection, scattering, and/or absorptive properties of interest.

The thicknesses and spacing of layers 102 and 104 may be determined using a variety of approximation methods based upon a conventional spectroscopic measurement of the characteristic of interest. These methods may include inverse Fourier transform (IFT) of the optical transmission spectrum, for example, and structuring ICE 100 as a physical representation of the IFT. The approximations convert the IFT into a structure based on known materials with constant refractive indices. Further information regarding the structures and design of exemplary integrated computational elements (also referred to as multivariate optical elements) is provided in *Applied Optics*, Vol. 35, pp. 5484-5492 (1996) and Vol. 29, pp. 2876-2893 (1990), which is incorporated by reference herein.

As previously discussed, layers 102 and 104 of ICE 100 exhibit different refractive indices. By properly selecting the materials of layers 102 and 104 and their relative spacing, ICE 100 may be configured to selectively transmit or reflect predetermined fractions of electromagnetic radiation at different wavelengths. A predetermined weighting coefficient or loading factor may be assigned to ICE 100 at each wavelength for transmission and reflection, thereby describing an optical function for each. Unless otherwise noted, it should be recognized that any analysis described herein based upon a transmission function may be made in a like manner using a reflection function, an absorption function, or dispersion function.

The weightings may be referred to as a regression vector of the characteristic being analyzed. ICE 100 may be configured to calculate the dot product of the regression vector based upon the electromagnetic radiation input upon the ICE. As a result, the output electromagnetic radiation intensity of ICE 100, which is captured by a detector, is related to the characteristic of interest. Further details regarding how ICE 100 is able to distinguish and process electromagnetic radiation related to a characteristic of interest are described in, for example, commonly owned U.S. Pat. No. 6,198,531, previously incorporated herein by reference in its entirety.

In some embodiments, devices described herein may comprise an optional electromagnetic radiation source; a sample detection unit comprising an integrated computational element and a detector that is configured to receive electromagnetic radiation that has optically interacted with the integrated computational element and produce a sample signal associated therewith; an interferent monitor located proximal to the sample detection unit, the interferent monitor being configured to produce an interferent signal associated with an interferent substance; and a signal processing unit that is operable to convert the interferent signal into an interferent input form suitable for being computationally combined with the sample signal, the signal processing unit being further operable to computationally combine the sample signal and the interferent input form to determine a characteristic of a sample in real-time or near real-time. In some embodiments, the devices may further comprise a data storage unit that is operable to record the sample signal and the interferent signal as a function of time.

In some embodiments, devices described herein may comprise an optional electromagnetic radiation source; a sample detection unit comprising a first integrated computational element and a detector that is configured to receive electromagnetic radiation that has optically interacted with the first integrated computational element and produce a sample signal associated therewith; an interferent monitor located proximal to the sample detection unit, the interferent monitor comprising a second integrated computational element and being configured to produce an interferent signal associated with an interferent substance or an interferent condition; an optional data storage unit that is operable to record the sample signal and the interferent signal as a function of time; and a signal processing unit that is operable to convert the interferent signal into an interferent input form suitable for being computationally combined with the sample signal, the signal processing unit being further operable to computationally combine the sample signal and the interferent input form to determine a characteristic of a sample. In some embodiments, the signal processing unit may be operable to determine the characteristic of the sample in real-time or near real-time.

The electromagnetic radiation optically interacting with the integrated computational element(s) of the devices described herein may come from any suitable source. In some embodiments, the electromagnetic radiation may come from an electromagnetic radiation source that is configured to impart electromagnetic radiation upon a sample and/or the integrated computational element(s). That is, in such embodiments, the source of electromagnetic radiation may be part of the device itself. In some or other embodiments, the electromagnetic radiation may be emitted by the sample or a material near the sample. This electromagnetic radiation may optically interact with the sample and/or the integrated computational element(s) to achieve a like result to that obtained using a separate electromagnetic radiation source. One of ordinary skill in the art will recognize various means through which a sample or other material may emit electromagnetic radiation. For example, through heating, a material may emit blackbody radiation that can optically interact with the integrated computational element(s) of the devices described herein. In other embodiments, a material may emit electromagnetic radiation by being radioactive or chemiluminescent, for example. In yet other embodiments, electromagnetic radiation may be emitted from a material in response to mechanical, magnetic, and/or electrical interaction with the material. For example, in some embodiments, an electrical potential may be placed across a sample in order to induce the production of electromagnetic radiation therefrom. Thus, an electromagnetic radiation source may be an optional feature in the devices described herein.

In some embodiments, the sample detection unit may contain one integrated computational element. In some embodiments, the sample detection unit may contain two or more integrated computational elements. Likewise, when an integrated computational element is used in the interferent monitor, one integrated computational element may be used in some embodiments, or two or more integrated computational elements may be used in other embodiments. When two or more integrated computational elements are used in either location, each integrated computational element may be used to analyze for a single characteristic or interferent (i.e., in a one-to-one relationship) in some embodiments. That is, in such embodiments, the integrated computational elements may be used essentially independently of one another. In other embodiments, the output of two or more integrated computational elements may be computationally combined to analyze for a single characteristic or interferent. As discussed above, when the output of two or more integrated computational elements is computationally combined, unexpectedly improved detection performance may be realized, as described in Applicant's copending applications filed concurrently herewith.

Furthermore, when two or more integrated computational elements are used in computational combination to analyze for an interferent or a characteristic of interest, the integrated computational elements may be associated with the interferent or characteristic of interest, disassociated with the interferent or characteristic of interest, or any combination thereof. As used herein, an integrated computational element that is associated with a characteristic is generally predictive of the characteristic when used alone. As described above, integrated computational elements have heretofore been specifically designed to be associated with a characteristic by varying their respective layers, thicknesses, and materials so as to correspond with the spectral attributes associated with the characteristic of interest. Although two or more integrated computational elements may be associated with a characteristic of interest, they may be designed differently from each other, if desired, thereby approximating or otherwise mimicking the regression vector of the characteristic of interest in entirely different ways.

In other embodiments in which two or more integrated computational elements are used in computational combination to analyze for an interferent or a characteristic of interest, some of the integrated computational elements may be associated with the interferent or characteristic of interest, and some of the integrated computational elements may be disassociated with the interferent or characteristic of interest. As used herein, an integrated computational element that is disassociated with a characteristic is substantially non-predictive of the characteristic when used alone. In some embodiments, each of the integrated computational elements may be disassociated with the interferent or characteristic of interest. Although one or more of the integrated computational elements may be disassociated with the interferent or characteristic of interest in the foregoing embodiments, once the outputs of each integrated computational element have been computationally combined according to the present embodiments, the combined result may be generally predictive for the interferent or characteristic of interest.

Furthermore, when two or more integrated computational elements are used in computational combination with one another, the integrated computational elements may each demonstrate a positive (i.e., increasing) response as a value of the characteristic increases, in some embodiments. In other embodiments, the integrated computational elements may each demonstrate a negative (i.e., decreasing) response as a value of the characteristic increases. In still other embodiments, at least some of the integrated computational elements may demonstrate a positive response and at least some of the integrated computational elements may demonstrate a negative response. As described in Applicant's copending applications filed concurrently herewith, when a combination of integrated computational elements having positive and negative responses is used for detection of a characteristic of interest, unexpected improvements in detection performance may be realized in some cases.

Although the integrated computational element(s) or combinations thereof may be configured to analyze for a characteristic of interest, they may still be subject to interference from interferent substances or interferent conditions, as described above. For example, in some embodiments, an interferent substance may block all or part of the electromagnetic radiation that is incident upon a sample and/or the integrated computational element(s). In other embodiments, an interferent substance or interferent condition may alter the performance of an integrated computational element. In still other embodiments, an interferent substance or interferent condition may interact with an electronic component of an optical computing device to change its performance (e.g., detector gain or other electronic performance parameter). Thus, if an interferent is present, particularly outside of normally expected ranges, the calibration associated with determining the characteristic may be impacted.

In some embodiments, the devices described herein may be configured to analyze and correct for the presence of one or more interferent substances. In some embodiments, the devices described herein may be further configured to analyze and correct for one or more interferent conditions, particularly temperature. For example, in some embodiments, the devices may also comprise a temperature sensor located proximal to the sample detection unit. In some embodiments, the temperature sensor may comprise a thermocouple or a pyrometer, for example. In such embodiments, the signal processing unit may be further operable to convert an output of the temperature sensor into a temperature input form suitable for being computationally combined with the sample signal, the signal processing unit being still further operable to computationally combine the sample signal, the interferent input form, and the temperature input form to determine a characteristic of a sample.

As discussed above, the presence of interferents may impact the performance of the devices described herein. In some embodiments, the sample detection unit may be placed in a protected environment that limits its exposure to interferent substances and/or interferent conditions. For example, in some embodiments, the sample detection unit and the interferent monitor may be located within a sealed container. In some embodiments, the sealed container or an aperture thereon may be at least partially transparent to electromagnetic radiation having a given wavelength or range of wavelengths, specifically electromagnetic radiation that has optically interacted with or that has been emitted by a sample. In some embodiments, the sealed container may contain a fixed environment in which the sample detection unit has a known performance for determining a characteristic of interest. That is, the sample detection unit may be held within calibration when it is maintained within the fixed atmosphere. The interferent monitor may be used in these embodiments to evaluate the integrity of the fixed environment, for example, in order to determine if a need exists to correct the output of the sample detection unit or otherwise further analyze data produced therefrom. In other embodiments, the interferent monitor may be used to analyze for interferent substances and/or interferent conditions that are external to the sealed container, in the sample or near the sample, for example. In either case, if interferents are within normal calibration ranges, the sample signal of the sample detection unit need not necessarily be corrected, although it may be corrected in real-time or near real-time, if desired, as described above, after converting the interferent signal into an appropriate interferent input form suitable for being computationally combined with the sample signal. Similar considerations may be made in embodiments in which the sample detection unit and interferent monitor are not located within a sealed container.

The types of interferent monitors usable in the devices described herein are not believed to be particularly limited. In some embodiments, the interferent monitor may comprise a sensor, such as a chemical sensor, for example. Various types of sensors suitable for detecting and quantifying interferent substances and/or interferent conditions will be familiar to one having ordinary skill in the art. In some embodiments, the interferent monitor may comprise a water sensor (e.g., a moisture sensor or a humidity sensor). In some embodiments, the interferent monitor may comprise a gas sensor (e.g., an oxygen sensor, a carbon dioxide sensor, a carbon monoxide sensor, a hydrogen sulfide sensor, a methane sensor, and the like). In some embodiments, the interferent monitor may comprise a particulate sensor. In some embodiments, the interferent monitor may comprise an ionizing radiation sensor. In some embodiments, the interferent monitor may comprise a magnetic field sensor. As one of ordinary skill in the art will appreciate, these types of sensors are typically inexpensive, rugged, and lacking in complicated electronics. These factors may make them well suited for use in the devices described herein. In some embodiments, a conventional spectrometer may be used as the interferent monitor. In still other embodiments, the interferent monitor may comprise one or more integrated computational elements. In some embodiments, a temperature sensor, when present, may comprise an integrated computational element.

According to the present embodiments, a sample signal from the sample detection unit may be corrected using an interferent signal associated with an interferent substance or interferent condition. As one of ordinary skill in the art will appreciate, the interferent signal produced by the interferent monitor may not necessarily be in a form suitable for being directly combined with the sample signal. For example, the sample signal may be a detector voltage associated with a characteristic of interest, and the interferent signal may be a voltage output of a sensor. Although both may be voltages, the signals may not be directly combinable, since they are associated with completely different electronic components. Therefore, the interferent signal may need to be converted into an interferent input form that is suitable for being computationally combined with the sample signal.

In various embodiments, the signal processing unit may be operable to convert the interferent signal into an interferent input form that is suitable for being computationally combined with the sample signal. Likewise, in some embodiments, the signal processing unit may be operable to convert an output of a temperature sensor, when present, into a temperature input form that is suitable for being computationally combined with the sample signal.

Converting the interferent signal into an interferent input form may comprise developing a correlation between an output of the sample detection unit and an output of the interferent monitor that is made using calibration standards having varying amounts of interferent substances and varying values of the characteristic of interest. As described above, the correction factor is a complex, multivariate function, and sufficient data should be collected to adequately understand the influence of the various parameters upon one another. Analysis of the calibration standards under a range of potential interfering conditions (e.g., temperature) may also be conducted. Specifically, each standard may be analyzed by the sample detection unit and the interferent monitor, and a correlation may be made between the output of the two. In some embodiments, the correlation may be developed as a lookup table. In other embodiments, the correlation may be developed as a function that describes the relationship of the various parameters to one another. Once the correlation is available, one would measure the characteristic of a sample using the sample detection while also measuring an interferent with the interferent monitor. Knowing the output of the interferent monitor, the output of the sample detection unit may be corrected (e.g., using Formulas 1 and 2 to perform a computational combination) to correct its output such that it is more representative of the true value of the characteristic. By performing the correlation and computational combination using the signal processing unit (i.e., through appropriate computational methodology), the sample signal may be corrected in real-time or near real-time to determine a characteristic of a sample.

In various embodiments, the computational combination described herein may take place in a signal processing unit such as a computer, for example, which may be operating an algorithm suitable for performing the computational combination and determining a sample characteristic. In some embodiments, the algorithm may be configured to make predictions on how a bulk characteristic of the sample changes if the concentrations of one or more parameters are changed relative to one another. That is, in some embodiments, the algorithm may be configured to make predictions of an unmeasured characteristic based upon a value obtained for one or more directly measured characteristics. In some embodiments, the algorithm can produce an output that is readable by an operator who can manually take appropriate action, if needed, based upon the output. In some embodiments, the algorithm can take proactive control of a process in which the devices are used by automatically adjusting the characteristic in response to an out-of-range condition. The algorithm may include training that dictates how an out-of-range condition may most suitably be dealt with.

In some embodiments, the algorithm can be part of an artificial neural network configured to use the concentration of each detected analyte in order to evaluate the characteristic(s) of the sample and predict how to modify the sample to alter its properties in a desired way. Illustrative but non-limiting artificial neural networks suitable for use in the present embodiments are described in commonly owned United States Patent Application Publication 2009/0182693, which is incorporated herein by reference in its entirety. It is to be recognized that an artificial neural network can be trained using standards having known concentrations, compositions, and/or properties (e.g., characteristics), thereby generating a virtual library. As the virtual library available to the artificial neural network becomes larger, the network can become more capable of accurately predicting the characteristics of a sample.

It is to be recognized that the various embodiments herein relating to computer control and artificial neural networks, including various blocks, modules, elements, components, methods, algorithms, and the like can be implemented using computer hardware, software, combinations thereof, and the like. To illustrate this interchangeability of hardware and software, various illustrative blocks, modules, elements, components, methods, algorithms, and the like have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the scope of the embodiments expressly described.

Computer hardware used to implement the various illustrative blocks, modules, elements, components, methods, algorithms, and the like described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory [e.g., random access memory (RAM), flash memory, read only memory (ROM), programmable read only memory (PROM), erasable read only memory (EPROM)], registers, hard disks, removable disks, CD-ROMS, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

In some embodiments, the data collected using the optical computing devices can be archived along with data associated with operational parameters being logged at a job site. Evaluation of job performance can then be assessed and improved for future operations or such information can be used to design subsequent operations. In addition, the data and information can be communicated (wired or wirelessly) to a remote location by a communication system (e.g., satellite communication or wide area network communication) for further analysis. The communication system can also allow remote monitoring and operation of a process to take place. Automated control with a long-range communication system can further facilitate the performance of remote job operations. In particular, an artificial neural network can be used in some embodiments to facilitate the performance of remote job operations. That is, remote job operations can be conducted automatically in some embodiments. In other embodiments, however, remote job operations can occur under direct operator control, where the operator is not at the job site.

In some embodiments, principal component analysis techniques may be used in the analysis by the signal processing unit. Such techniques can include partial least squares analysis, for example. The principal component analysis may be conducted using standard statistical analysis software packages including, for example, XL Stat for MICROSOFT® EXCEL®, the UNSCRAMBLER® from CAMO Software, and MATLAB® from MATHWORKS®).

The electromagnetic radiation that has optically interacted with the integrated computational element(s) may be received by one or more detectors. In some embodiments, there may be a separate detector configured to receive electromagnetic radiation that has optically interacted with each integrated computational element. In some embodiments, a single detector may be configured to receive electromagnetic radiation from multiple integrated computational elements, although not at the same time. Thus, a signal may be produced from each integrated computational element as a function of time. Detectors suitable for analyzing various types of electromagnetic radiation will be familiar to one having ordinary skill in the art, any of which may be used in the various embodiments described herein. Illustrative detectors that may be used in the various embodiments described herein may include, for example, thermal detectors (e.g., thermopile or photoacoustic detectors), semiconductor detectors, piezoelectric detectors, charge-coupled device (CCD) detectors, video or array detectors, split detectors, photon detectors (e.g., photomultiplier tubes), photodiodes and photodiode arrays, any combination thereof, and the like. In addition, any other type of detector known to one having ordinary skill in the art may also be used.

When the sample detection unit comprises a first integrated computational element and the interferent monitor comprises a second integrated computational element, the sample detection unit may comprise a first detector and the interferent monitor may comprise a second detector, in some embodiments, where the second detector is configured to receive electromagnetic radiation that has optically interacted with the second integrated computational element. In some embodiments, the electromagnetic radiation that has optically interacted with the first integrated computational element and the second integrated computational element may be received by the same detector, but not at the same time. In some embodiments, a first detector may receive electromagnetic radiation that has optically interacted with a first integrated computational element, and a second detector may receive electromagnetic radiation that has optically interacted with the second integrated computational element.

The devices of the present disclosure will now be described in greater detail herein with reference to the drawings. Although the following FIGURES all depict an electromagnetic radiation source, it is to be recognized that the electromagnetic radiation that optically interacts with the integrated computational element(s) may be emitted by the sample or a material near the sample, as discussed above, and its use may therefore be optional. Further, although certain devices of the following FIGURES are depicted as being housed in a container, it is to be recognized that a container is an optional feature, and the devices may be configured to be placed directly in or near a sample being analyzed. It is also to be recognized that the configurations depicted in the following FIGURES are meant to be illustrative in nature and should therefore be considered non-limiting. Various alternative configurations, modifications of the depicted configurations, and combinations thereof may be envisioned by one having ordinary skill in the art.

In the FIGURES that follow, electromagnetic radiation that has not optically interacted with an integrated computational element has been depicted with solid, single-headed arrows. Electromagnetic radiation that has optically interacted with an integrated computational element has been depicted with dashed, single-headed arrows. Signals produced from a detector or an interferent monitor and fed to a signal processing unit are depicted with dashed, double-headed arrows. Although not specifically shown in any of the following FIGURES, one or more spectral elements may be included in the devices in order to restrict the optical wavelengths and/or bandwidths of the system and thereby eliminate unwanted electromagnetic radiation existing in wavelength regions that have little or no importance. Such spectral elements can be located anywhere along the optical train, but are often employed immediately after the electromagnetic radiation source, if present. Illustrative spectral elements suitable for use in the devices described herein may be found in the commonly owned United States patents and patent application Publications previously incorporated by reference herein.

Figure 2:
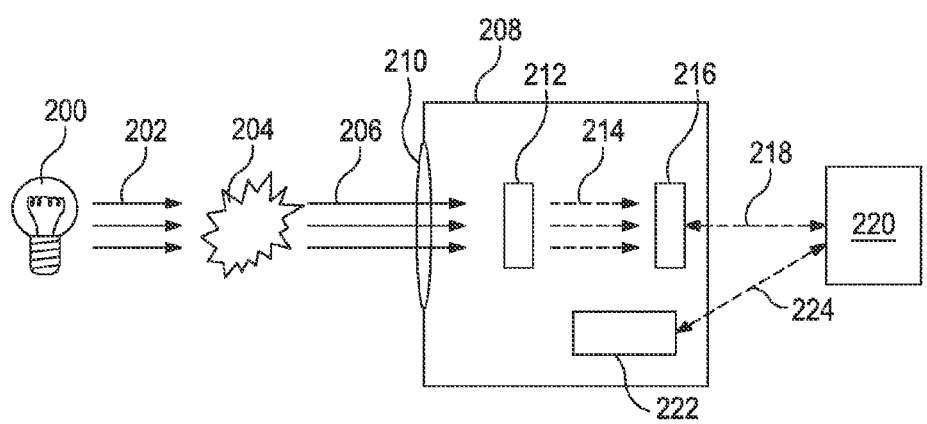
FIG. 2 shows a schematic of an illustrative optical computing device containing an integrated computational element and an interferent monitor computationally linked to a signal processing unit.

FIG. 2 shows a schematic of an illustrative optical computing device containing an integrated computational element and an interferent monitor computationally linked to a signal processing unit. As shown in FIG. 2, source 200 provides electromagnetic radiation 202, which is illuminated on sample 204. After optically interacting with sample 204, sample-interacted electromagnetic radiation 206, enters container 208 via optically transparent aperture 210, where it then optically interacts with integrated computational element 212 to produce optically interacted electromagnetic radiation 214. Optically interacted electromagnetic radiation 214 is then directed upon detector 216, which produces sample signal 218 associated with a characteristic of interest in sample 204. Sample signal 218 is then fed to signal processing unit 220 for further manipulation such that an output regarding a characteristic of interest is produced. Meanwhile, interferent monitor 222, which is located in container 208 in proximity to integrated computational element 212, monitors for the presence of interferents therein and produces interferent signal 224, which is also fed to signal processing unit 220.

Figure 3A:
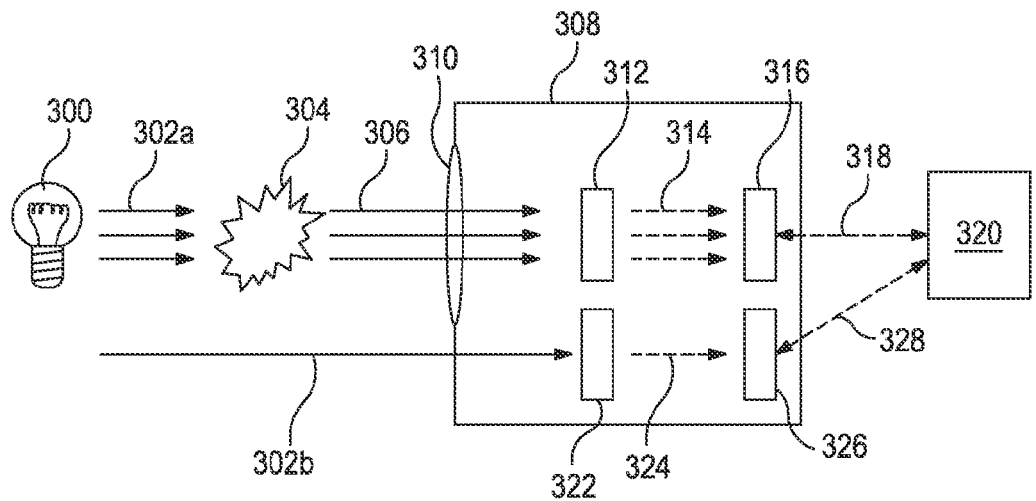
FIGS. 3A and 3B show schematics of an illustrative optical computing device containing a first integrated computational element for monitoring a characteristic of interest and a second integrated computational element for monitoring an interferent.
Figure 3B:
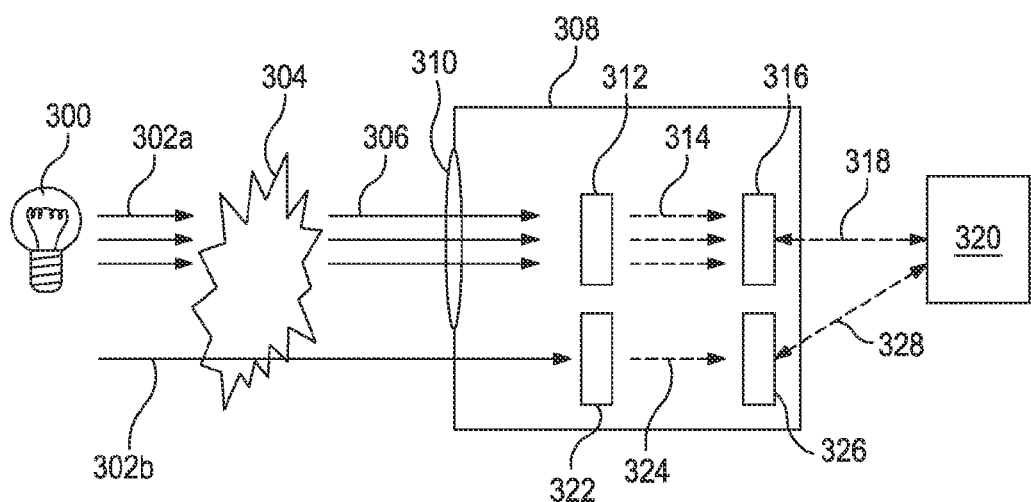

FIGS. 3A and 3B show schematics of an illustrative optical computing device containing a first integrated computational element for monitoring a characteristic of interest and a second integrated computational element for monitoring an interferent. As depicted in FIGS. 3A and 3B, source 300 provides electromagnetic radiation 302a, which is illuminated on sample 304, and electromagnetic radiation 302b, which need not necessarily illuminate sample 304. Electromagnetic radiation 302b is ultimately used to analyze for the presence of an interferent, which may be present in sample 304 or a region surrounding sample 304. Accordingly, electromagnetic radiation 302b may optically interact with the sample in some embodiments (FIG. 3B) or not optically interact with the sample in other embodiments (FIG. 3A). After optically interacting with sample 304, sample-interacted electromagnetic radiation 306, enters container 308 via optically transparent aperture 310, where it then optically interacts with first integrated computational element 312 to produce optically interacted electromagnetic radiation 314. Optically interacted electromagnetic radiation 314 is then directed upon first detector 316, which produces sample signal 318 associated with a characteristic of interest in sample 304. Sample signal 318 is then fed to signal processing unit 320 for further manipulation. Meanwhile, electromagnetic radiation 302b also enters container 308 via aperture 310. Electromagnetic radiation 302b then optically interacts with second integrated computational element 322 to produce optically interacted electromagnetic radiation 324. Optically interacted electromagnetic radiation 324 is directed to second detector 326, which produces interferent signal 328 associated with an interferent substance or interferent condition. Interferent signal 328 is then fed to signal processing unit 320 for computational combination with sample signal 318.

Figure 4:
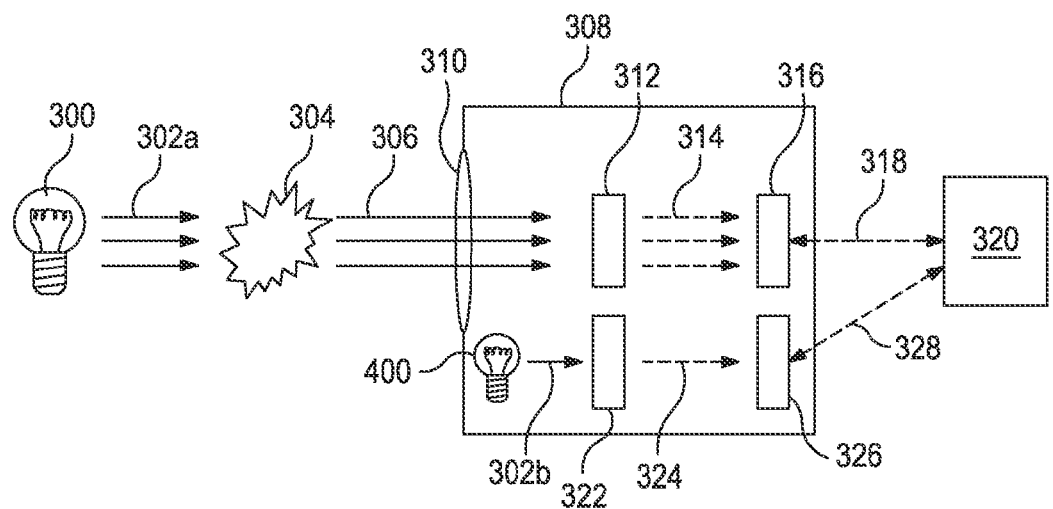
FIG. 4 shows a schematic of an illustrative optical computing device depicting an alternative configuration of the devices FIGS. 3A and 3B.

FIG. 4 shows a schematic of an illustrative optical computing device depicting an alternative configuration of the devices FIGS. 3A and 3B. In FIG. 4, instead of supplying electromagnetic radiation 302a and 302b from a single source, electromagnetic radiation 302a may be supplied to sample 304 from source 300, and electromagnetic radiation 302b may be supplied to second integrated computational element 322 from source 400. As depicted in FIG. 4, source 400 may be located within container 308 so as to monitor for the presence of an interferent therein. Like reference characters are used in FIG. 4 to depict those elements that are substantially the same as those described and depicted in FIGS. 3A and 3B.

Figure 5:
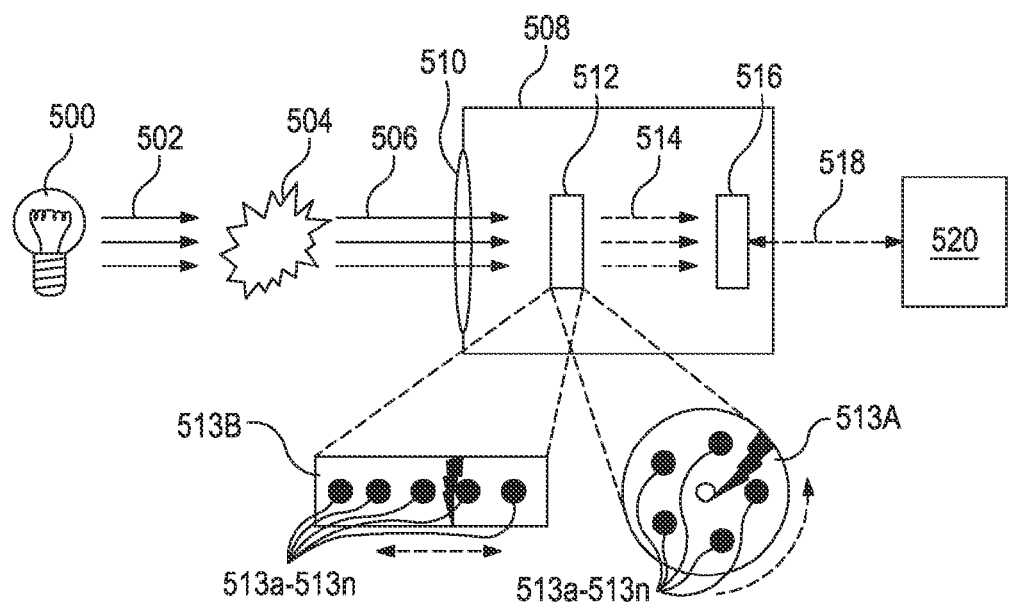
FIG. 5 shows a schematic of an illustrative optical computing device depicting an alternative configuration of the devices of FIGS. 3A and 3B in which a single detector is used.

FIG. 5 shows a schematic of an illustrative optical computing device depicting an alternative configuration of the devices of FIGS. 3A and 3B in which a single detector is used. When a single detector is used, as in FIG. 5, the sample signal and the interferent signal may be time multiplexed at the detector to determine each signal. As depicted in FIG. 5, source 500 provides electromagnetic radiation 502, which is illuminated on sample 504 to produce sample-interacted electromagnetic radiation 506. Sample-interacted electromagnetic radiation 506 enters container 508 via optically transparent aperture 510, where it interacts sequentially in time with integrated computational elements 513a-513n located on movable assembly 512. Movable assembly 512 is configured to rotate or translate integrated computational elements 513a-513n as a function of time, such that generally only one integrated computational element is producing optically interacted electromagnetic radiation 514 at any given time. Optically interacted electromagnetic radiation 514 is conveyed to detector 516, which produces time multiplexed signal 518 that is fed to signal processing unit 520. Since different integrated computational elements are optically interacting with electromagnetic radiation at different points in time, signal 518 resulting from optically interacted electromagnetic radiation 514 also varies as a function of time. Thus, time multiplexed signals 518 from detector 516 may be computationally combined by signal processing unit 520. It is to be recognized that any number, n, of integrated computational elements greater than or equal to 2 may be present on movable assembly 512. At least some of integrated computational elements 513a-513n may be configured to analyze for a characteristic of interest, singularly or in combination, and at least some of integrated computational elements 513a-513n may be configured to analyze for an interferent. In some embodiments, movable assembly 512 may be characterized as rotating disk 513A, having integrated computational elements 508a-508n radially disposed thereon. In other embodiments, movable assembly 512 may be characterized as linear array 513B, having integrated computational elements 508a-508e laterally offset thereon. During operation of the devices, movable assembly 512 may be cycled at any suitable rate. For example, when rotating disk 513A is used, the rotation rate may range between about 0.1 rpm to about 30,000 rpm in order to produce signal 518 that varies with time.

Although FIGS. 2-4 have depicted a single integrated computational element being optically interacted with electromagnetic radiation to assay a characteristic of interest and/or an interferent, it is to be recognized that the outputs of more than one integrated computational element may be computationally combined to accomplish a like purpose. FIG. 5 shows one such configuration whereby the outputs of more than one integrated computational element may be computationally combined by a signal processing unit. FIGS. 6-10 show illustrative schematics demonstrating several additional ways in which two or more integrated computational elements may be configured for being computationally combined to analyze for a characteristic of interest or an interferent. For the sake of simplicity, FIGS. 6-10 have focused on the configuration of the integrated computational elements and the detectors relative to one another. However, it is to be recognized that the depicted configurations employing two or more integrated computational elements may be incorporated in the devices generally described and depicted hereinabove by one having ordinary skill in the art. Further, it is to be recognized that combinations of integrated computational elements may be used to analyze for a characteristic of interest, an interferent, or both.

Figure 6:
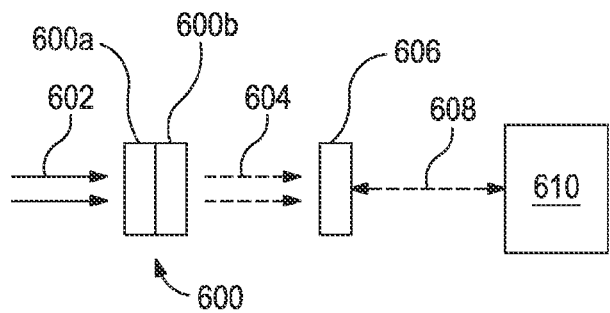
FIG. 6 shows an illustrative schematic demonstrating how two integrated computational elements may be combined as a monolithic structure to result in their direct computational combination.

FIG. 6 shows an illustrative schematic demonstrating how two integrated computational elements 600a and 600b may be combined as a monolithic structure 600 to result in their direct computational combination. As depicted in FIG. 6, electromagnetic radiation 602 optically interacts with monolithic structure 600 to produce optically interacted electromagnetic radiation 604, which is directed to detector 606 to produce signal 608 associated therewith. Signal 608 may then be fed to signal processing unit 610 for determination of a characteristic of interest. It is to be noted that in the configuration depicted in FIG. 6, the output (i.e., signal 608) of integrated computational elements 600a and 600b is already computationally combined, rather than a computation that takes place separately by combining discrete signals.

Figure 7:
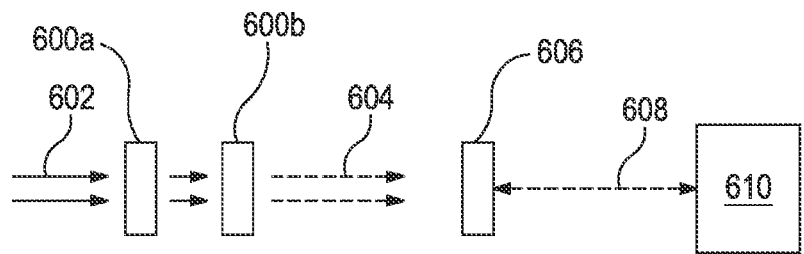
FIG. 7 shows an illustrative schematic demonstrating how two integrated computational elements may be disposed in series to result in their direct computational combination.

In an alternative configuration to that generally depicted in FIG. 6, the two integrated computational elements may be disposed in series rather than being incorporated as a monolithic structure. FIG. 7 shows an illustrative schematic demonstrating how two integrated computational elements 600a and 600b may be disposed in series to result in their direct computational combination. Like reference characters have been used in FIG. 7 to depict features corresponding to those in FIG. 6. Accordingly, those features will not be described again in detail.

Figure 8:
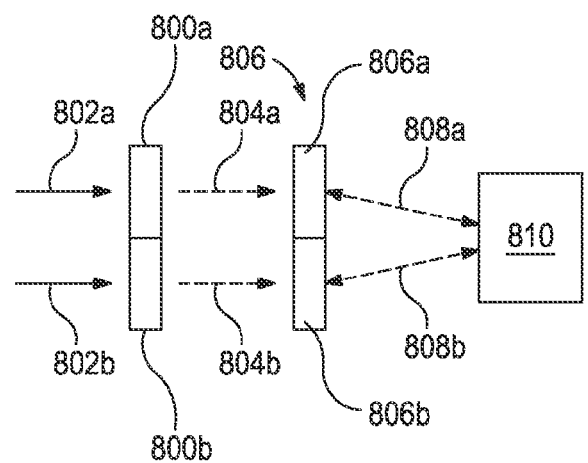
FIGS. 8-10 show illustrative schematics demonstrating how two integrated computational elements may be disposed generally in parallel to one another to produce separate signals at a first detector and a second detector.
Figure 9:
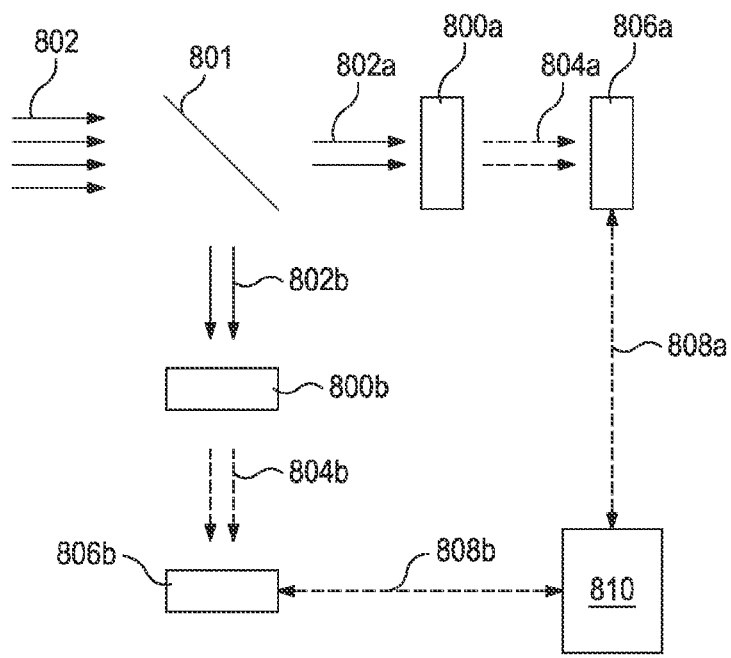
Figure 10:
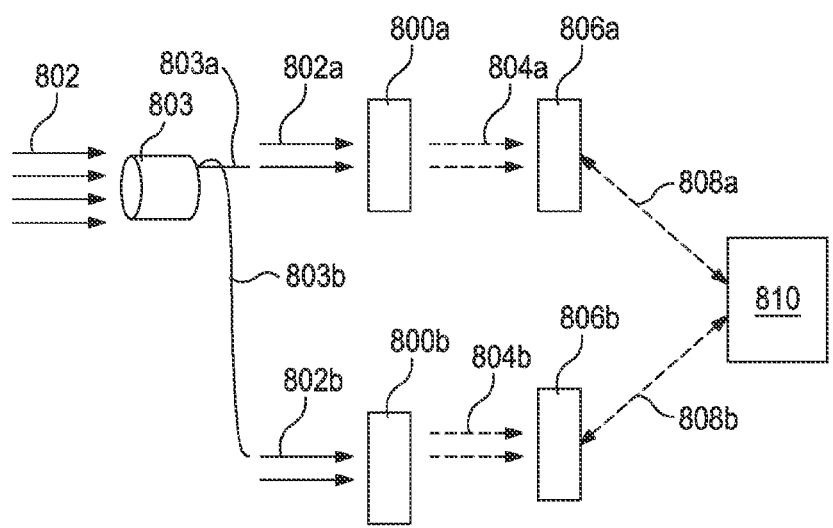

The output of two or more integrated computational elements may also be computationally combined using the output of two or more separate detectors, as generally depicted above in FIGS. 3A and 3B, for example. That is, electromagnetic radiation may optically interact with two or more integrated computational elements that are generally parallel (i.e., adjacent) to one another and optically interacted electromagnetic radiation may be directed to two or more separate detectors. It is to be recognized that the direction of electromagnetic radiation within an optical computing device may be accomplished using any technique known to one having ordinary skill in the art. For example, in various embodiments, electromagnetic radiation may be directed using any combination of beam splitters, mirrors, optical fibers, and the like. FIGS. 8-10 show illustrative schematics demonstrating how two integrated computational elements may be disposed generally in parallel to one another to produce separate signals at a first detector and a second detector, respectively.

As depicted in FIGS. 8-10, electromagnetic radiation portion 802a may impinge upon integrated computational element 800a to produce optically interacted electromagnetic radiation 804a, and electromagnetic radiation portion 802b may impinge upon integrated computational element 800b to produce optically interacted electromagnetic radiation 804b. In FIG. 8, the interaction of electromagnetic radiation portions 802a and 802b upon the integrated computational elements is direct. That is, there is no beam splitting or diversion of the incident electromagnetic radiation depicted. Although FIG. 8 has depicted integrated computational elements 800a and 800b as touching one another, they may be spaced apart and/or offset, if desired. Likewise, detector 806, containing first detector 806a and second detector 806b may be spaced apart, if desired. As depicted in FIGS. 9 and 10, a parent beam of electromagnetic radiation 802 may be subdivided to produce electromagnetic radiation portions 802a and 802b. In FIG. 9, beam splitter 801 may be used to subdivide electromagnetic radiation 802 into electromagnetic radiation portions 802a and 802b. In FIG. 10, optical pipe 803 containing a plurality of optical filaments may be used to subdivide electromagnetic radiation 802 into electromagnetic radiation portions 802a and 802b. Specifically, optical filaments 803a may produce electromagnetic radiation portion 802a, and optical filaments 803b may produce electromagnetic radiation portion 802b. Regardless of how electromagnetic radiation portions 802a and 802b are produced, they may optically interact, respectively, with integrated computational elements 800a and 800b to produce optically interacted electromagnetic radiation 804a and 804b. Optically interacted electromagnetic radiation 804a and 804b may likewise be received by detectors 806a and 806b to produce signals 808a and 808b. Signals 808a and 808b may then be fed to and computationally combined by signal processing unit 810, as previously described above.

Although FIGS. 2-10 have generally shown electromagnetic radiation optically interacting with a sample before optically interacting with the integrated computational element(s), it is to be recognized that the embodiments depicted and described herein are not so limited in this manner. In any of the embodiments depicted and described herein, the sample may be located after the integrated computational element(s), such that optically interacted electromagnetic radiation illuminates the sample and is subsequently conveyed to one or more detectors.

Furthermore, although FIGS. 2-10 have generally depicted the optically interacted electromagnetic radiation as being transmitted electromagnetic radiation, it is to be recognized that reflected, diffusely reflected, scattered, or dispersed electromagnetic radiation may be detected and analyzed in a like manner using devices that are so configured. Likewise, electromagnetic radiation may be reflected from the sample, instead of being transmitted therethrough, as depicted.

In some embodiments, methods for analyzing a characteristic of a sample are described herein. In some embodiments, the methods may comprise detecting electromagnetic radiation that has optically interacted with at least one integrated computational element and correcting a sample signal produced therefrom. Specifically, the methods may comprise computationally combining the sample signal with an interferent signal or a form derived therefrom in order to produce a combined signal that may be correlated to a sample characteristic of interest.

In some embodiments, the methods described herein can comprise: providing electromagnetic radiation that has optically interacted with or that has been emitted by a sample; providing a sample detection unit comprising a first integrated computational element and a detector configured to receive electromagnetic radiation that has optically interacted with the first integrated computational element; optically interacting electromagnetic radiation with the first integrated computational element; detecting the electromagnetic radiation that has optically interacted with the first integrated computational element, thereby producing a sample signal associated therewith; monitoring an interferent substance using an interferent monitor and producing an interferent signal associated therewith; converting the interferent signal into an interferent input form suitable for being computationally combined with the sample signal; computationally combining the sample signal and the interferent input form so as to produce a combined signal; and correlating the combined signal to a characteristic of the sample in real-time.

In some embodiments, the interferent monitor may comprise a sensor such as a water sensor, a gas sensor, a particulate sensor, or any combination thereof, for example. In other embodiments, the interferent monitor may comprise one or more integrated computational elements that may be configured to analyze for an interferent substance or an interferent condition.

In some embodiments, the methods may further comprise monitoring a temperature of the sample detection unit using a temperature sensor, and converting an output of the temperature sensor into a temperature input form suitable for being computationally combined with the sample signal. In such embodiments, the combined signal may comprise a computational combination of the temperature input form. Discussion of how to convert an output of a sensor into a suitable input form has been generally described hereinabove.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

The invention claimed is:

1. A device comprising:
a sample detection unit comprising an integrated computational element and a detector, the integrated computational element being configured to analyze for a characteristic of interest in a sample based upon the dot product of a regression vector of the characteristic being analyzed, and the detector being positioned to receive electromagnetic radiation that has optically interacted with the integrated computational element and produce a sample signal associated with the received electromagnetic radiation;
an interferent monitor located proximal to the sample detection unit, the interferent monitor being configured to produce an interferent signal associated with an interferent substance; and
a signal processing unit that is operable to convert the interferent signal into an interferent input form suitable for being computationally combined with the sample signal, the signal processing unit being further operable to computationally combine the sample signal and the interferent input form to determine the characteristic of interest in real-time or near real-time.

2. The device of claim 1, wherein the sample detection unit and the interferent monitor are located within a sealed container.

3. The device of claim 1, wherein the interferent monitor comprises a sensor selected from the group consisting of a water sensor, a gas sensor, a particulate sensor, a magnetic sensor, an ionizing radiation sensor, and any combination thereof.

4. The device of claim 1, further comprising:
a temperature sensor located proximal to the sample detection unit;
wherein the signal processing unit is further operable to convert an output of the temperature sensor into a temperature input form suitable for being computationally combined with the sample signal, the signal processing unit being still further operable to computationally combine the sample signal, the interferent input form, and the temperature input form to determine the characteristic of interest.

5. The device of claim 1, further comprising:
a data storage unit that is operable to record the sample signal and the interferent signal as a function of time.

6. The device of claim 1, wherein the sample detection unit comprises two or more integrated computational elements, the integrated computational elements each producing outputs that are computationally combinable to determine the characteristic of interest.

7. A device comprising:
a sample detection unit comprising a first integrated computational element and a detector, the first integrated computational element being configured to analyze for a characteristic of interest in a sample based upon the dot product of a regression vector of the characteristic being analyzed, and the detector being positioned to receive electromagnetic radiation that has optically interacted with the first integrated computational element and produce a sample signal associated with the received electromagnetic radiation;
an interferent monitor located proximal to the sample detection unit, the interferent monitor comprising a second integrated computational element and being configured to produce an interferent signal associated with an interferent substance or an interferent condition;
an optional data storage unit that is operable to record the sample signal and the interferent signal as a function of time; and
a signal processing unit that is operable to convert the interferent signal into an interferent input form suitable for being computationally combined with the sample signal, the signal processing unit being further operable to computationally combine the sample signal and the interferent input form to determine the characteristic of interest.

8. The device of claim 7, wherein the signal processing unit is operable to determine the characteristic of the sample in real-time or near real-time.

9. The device of claim 7, wherein the sample detection unit comprises a first detector and the interferent monitor comprises a second detector, the second detector being configured to receive electromagnetic radiation that has optically interacted with the second integrated computational element.

10. The device of claim 7, wherein the detector is configured to receive electromagnetic radiation that has optically interacted with the second integrated computational element and electromagnetic radiation has optically interacted with the first integrated computational element, but not at the same time.

11. The device of claim 7, wherein the sample detection unit and the interferent monitor are located within a sealed container.

12. The device of claim 7, further comprising:
a temperature sensor located proximal to the sample detection unit;
wherein the signal processing unit is further operable to convert an output of the temperature sensor into a temperature input form suitable for being computationally combined with the sample signal, the signal processing unit being still further operable to computationally combine the sample signal, the interferent input form, and the temperature input form to determine the characteristic of interest.

13. The device of claim 12, wherein the signal processing unit is operable to determine the characteristic of the sample in real-time or near real-time.

14. The device of claim 12, wherein the temperature sensor comprises a third integrated computational element.

15. The device of claim 7, wherein the sample detection unit, the interferent monitor, or both comprises an additional integrated computational element, the additional integrated computational element producing an output that is computationally combinable with an output of the first integrated computational element or the second integrated computational element to determine a characteristic of a sample or an interferent substance or condition, respectively.

16. A method comprising:
providing electromagnetic radiation that has optically interacted with or that has been emitted by a sample;
providing a sample detection unit comprising a first integrated computational element and a detector, the first integrated computational element being configured to analyze for a characteristic of interest in the sample based upon the dot product of a regression vector of the characteristic being analyzed, and the detector being positioned to receive electromagnetic radiation that has optically interacted with the first integrated computational element;

optically interacting electromagnetic radiation with the first integrated computational element;

detecting the electromagnetic radiation that has optically interacted with the first integrated computational element, thereby producing a sample signal associated therewith;

monitoring an interferent substance using an interferent monitor and producing an interferent signal associated therewith;

converting the interferent signal into an interferent input form suitable for being computationally combined with the sample signal;

computationally combining the sample signal and the interferent input form so as to produce a combined signal; and correlating the combined signal to a characteristic of the sample in real-time or near real-time.

17. The method of claim 16, wherein the interferent monitor comprises a sensor selected from the group consisting of a water sensor, a gas sensor, a particulate sensor, a magnetic sensor, an ionizing radiation sensor, and any combination thereof.

18. The method of claim 16, further comprising:
monitoring a temperature of the sample detection unit using a temperature sensor; and
converting an output of the temperature sensor into a temperature input form suitable for being computationally combined with the sample signal;
wherein the combined signal further comprises a computational combination of the temperature input form.

19. The method of claim 16, wherein the interferent monitor comprises a second integrated computational element.

20. The method of claim 16, wherein the electromagnetic radiation optically interacts with the sample before optically interacting with the first integrated computational element.

21. The method of claim 16, wherein the electromagnetic radiation optically interacts with the sample after optically interacting with the first integrated computational element.

* * * * *